United States Patent
Godik

(12)
(10) Patent No.: US 6,243,484 B1
(45) Date of Patent: Jun. 5, 2001

(54) DYNAMIC-FUNCTIONAL IMAGING OF BIOLOGICAL OBJECTS USING A NON-RIGID OBJECT HOLDER

(75) Inventor: Eduard E. Godik, Suffern, NY (US)

(73) Assignee: DOBI Medical Systems, LLC, Mahwah, NJ (US)

( * ) Notice: Subject to any disclaimer, the term of this patent is extended or adjusted under 35 U.S.C. 154(b) by 0 days.

(21) Appl. No.: 09/399,306

(22) Filed: Sep. 20, 1999

Related U.S. Application Data

(63) Continuation of application No. PCT/US98/05559, filed on Mar. 20, 1998.
(60) Provisional application No. 60/041,034, filed on Mar. 21, 1997.

(51) Int. Cl.[7] ..................................... G06K 9/00
(52) U.S. Cl. .................. 382/128; 128/109.1; 250/491.1; 378/195
(58) Field of Search ..................... 382/128, 132; 128/109.1, 111.1; 250/459.1, 461.2, 491.1; 378/87, 86, 70, 145, 195; 450/1, 38; 600/310

(56) References Cited

U.S. PATENT DOCUMENTS

| | | | |
|---|---|---|---|
| 4,691,333 | 9/1987 | Gabriele et al. | 378/37 |
| 4,943,522 | 7/1990 | Eisinger et al. | 435/7 |
| 4,998,270 | 3/1991 | Scheid et al. | 378/155 |
| 5,204,253 | 4/1993 | Sanford et al. | 435/172.3 |
| 5,257,956 | 11/1993 | Ewen | 450/1 |
| 5,289,520 | 2/1994 | Pellegrino et al. | 378/37 |
| 5,305,365 | 4/1994 | Coe | 378/37 |
| 5,347,656 | 9/1994 | Fabritz et al. | 2/67 |
| 5,348,018 | 9/1994 | Alfano et al. | 128/665 |
| 5,349,954 | 9/1994 | Tiemann et al. | 128/634 |
| 5,467,767 | 11/1995 | Alfano et al. | 128/665 |
| 5,474,072 | 12/1995 | Shmulewitz | 128/660.09 |
| 5,499,989 | 3/1996 | LaBash | 606/130 |
| 5,553,111 | 9/1996 | Moore et al. | 378/37 |

*Primary Examiner*—Jay Patel
(74) *Attorney, Agent, or Firm*—Perkins, Smith & Cohen, LLP; Jacob N. Erlich; Jerry Cohen

(57) ABSTRACT

A non-rigid object holder assembly for use in examination of an object having a base (6), a first member (5) and a second member (2) movably mounted with respect to each other and said base (6), a mechanism (8) for controllably moving the members with respect to each other and the base. A first resilient membrane (4) attached to the first member (5) and a second resilient membrane (1) attached to the second member (2), the first and the second resilient membranes forming first and second inflatable components (4',1') for holding the object to be examined therebetween. A pressure system ((11, 19) operably connected to the first and the second inflatable components for controllably inflating each of the inflatable components. A source of electromagnetic radiation (14) optically associated with the inflatable components for providing a beam of light to the object and an optical detecting system (15) optically aligned with the source of electromagnetic radiation (14) for receiving said electromagnetic radiation passing through and/or being backscattered from the object.

31 Claims, 5 Drawing Sheets

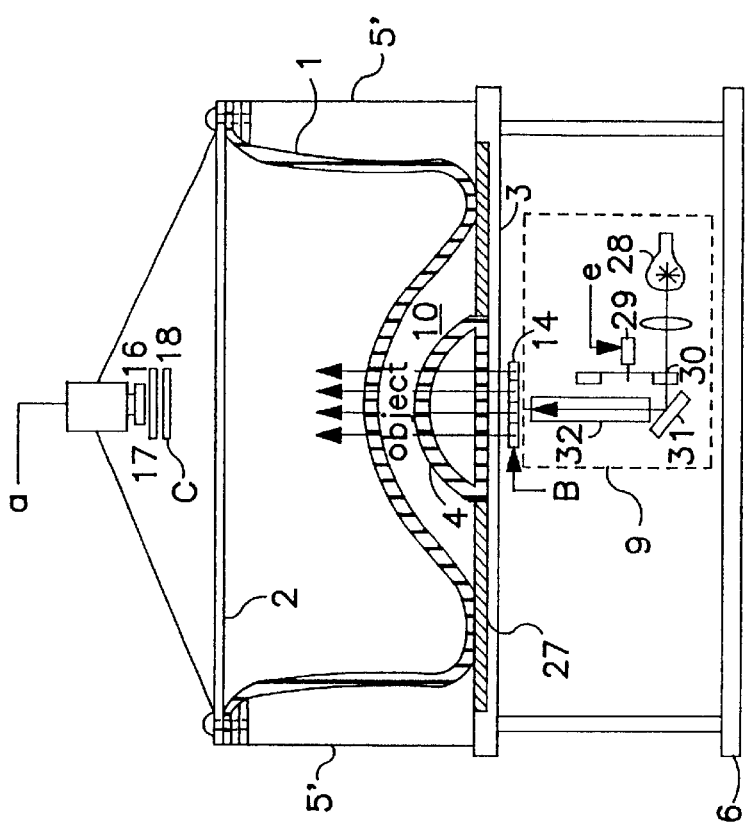
FIG. 2
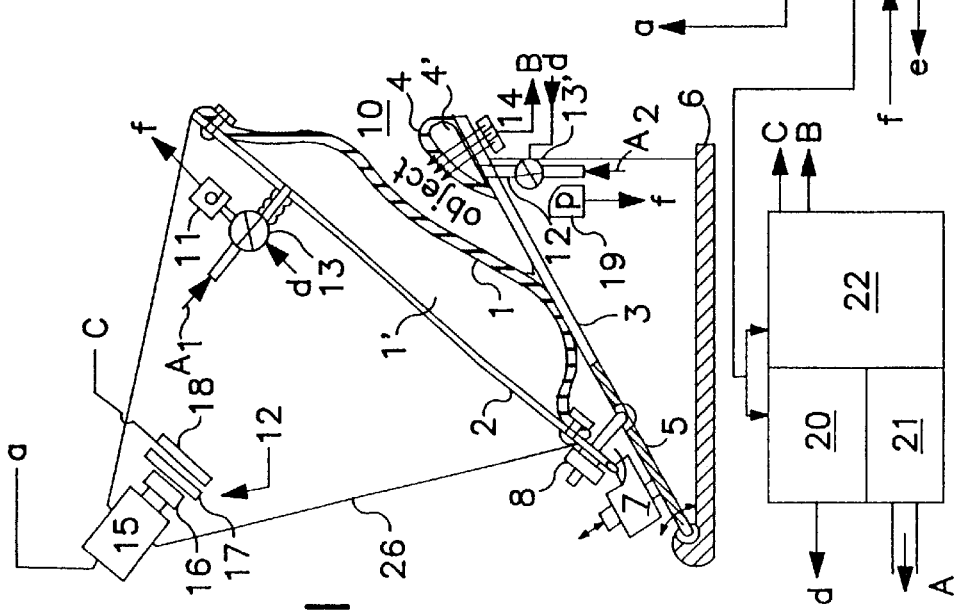
FIG. 1
FIG. 3

DYNAMIC-FUNCTIONAL IMAGING OF BIOLOGICAL OBJECTS USING A NON-RIGID OBJECT HOLDER

CROSS REFERENCE TO RELATED APPLICATIONS

This application is a continuation of PCT Application No. PCT/US98/05559, filed Mar. 20, 1998, entitled, "Dynamic-Functional Imaging of Biological Objects Using a Non-Rigid Object Holder." This application also claims priority of Provisional Application Ser. No. 60/041,034 filed Mar. 21, 1997 entitled "Dynamic-Functional Imaging of Biological Objects Using a Non-Rigid Object Holder."

FIELD OF THE INVENTION

This invention relates generally to dynamic functional imaging of biological objects and, more particularly, to the utilization of a non-rigid object holder in conjunction therewith, and, even more specifically, for use in the screening for breast cancer.

BACKGROUND OF THE INVENTION

One of the largest health problems facing the public today relates to cancer and devising safe and accurate screening procedures especially for breast cancer. There is a substantial difference between breast cancer diagnostics and breast cancer screening, in that breast cancer diagnostics are applied when a patient appears in a doctor's office or hospital with an already existing breast problem. Breast cancer screening relates to cancer detection prior to symptoms occurring. It is hoped with a proper breast cancer screening program that the treatment of breast cancer and potential breast cancer can take place at an early stage and, therefore, effect a high cure rate.

One of the common breast cancer screening procedures in use today involves the use of X-ray radiation during mammography as well as during breast cancer diagnostics with the utilization of stereotaxic mammography which is utilized to localize the pathology, and simultaneously perform a needle biopsy in conjunction therewith to identify the malignancy. Such screening and diagnostic techniques, based on revealing of morphological changes in the breast, many times comes about too late for appropriate treatment, is expensive to perform and in many instances is harmful to the patient by exposing them to X-ray radiation. Furthermore, since the diagnosis obtained through mammography results in a high rate of false positive diagnoses, approximately five times as many patients are exposed to unnecessary X-ray radiation than necessary.

An additional problem for the mammography application to breast cancer screening is the strong compression (up to 30 psi) of the breast between two rigid plates (holder) to immobilize the breast during examination to decrease x-ray scattering in breast tissue. This compression creates substantial discomfort as well as pain for the patient and may even be harmful since there is a danger of cancerous cells disseminating if a lesion is disrupted. In addition to this disadvantage of current techniques, the X-ray radiation itself may be harmful to the patient. Furthermore, another disadvantage of current mammography techniques is that the Xray radiation can reveal only morphological contrast.

Effective breast cancer screening should be safe and highly accurate in detecting cancers, and should be started from puberty. The procedure should be inexpensive and digital in operation so that comparison between personal results of multiple sequential examinations would be possible. To date, extensive use of such safe breast cancer screening procedures is not a practicality.

In another technique under development today involves optical mammoscopy with spectroscopy which investigates definite changes produced by cancer in the physiological patterns of tissues, dominantly in the steady state distributions of blood content, oxygenation and metabolic rate. This technique, however, is directed dominantly to achieving as high spatial resolution as in that in morphological imaging. The utilization of lasers to overcome strong multiple scattering of light in the biological tissues makes such a technique rather expensive and questionably safe for screening.

The present inventor has developed a dynamic functional imaging technique of the type described in U.S. patent application Ser. Nos. 08/565,747 and 08/678,786; and more specifically to an optical functional mammoscopy technique as described in U.S. patent application Ser. No. 08/664,189. In such a technique, more specifically denoted as dynamic functional optical mammoscopy (DFOM), near infrared radiation in the wave length range of 0.6–1.1 microns is utilized. This near infrared radiation is very similar to regular background illumination and, therefore, eliminates many of the problems associated with past devices which rely upon lasers. Further, the intensity applied (10–30 $mW/cm^2$) is comparable with that of background thermal infrared radiation. Consequently, the utilization of DFOM is absolutely safe. Further, this technique applies the transient functional patterns of tissues with the pixels being temporal signatures of spontaneous tissue functioning and reactivities in response to selected stimuli which are reflective of a whole organ's synergy. Such an approach is extremely effective for the examination of mammary glands or breasts characterized by high symmetrical physiological functioning and structure, biologically directed to the nipple. In this case, temporal sequences of optical images are recorded. To obtain the specificity of the temporal signatures necessary for pathology transient pattern recognition, the interframe intervals should be differentially small against the time constant of the physiological process.

One drawback to such a dynamic functional optical mammoscopy technique is the utilization to date of hard or rigid holders therewith. The same difficulties encountered by the use of such rigid holders in past techniques also constitute a problem when utilized with the dynamic functional optical mammoscopy technique. It is therefore necessary to develop in conjunction with such a dynamic functional optical imaging system a holder which can form an integral part thereof, be reliable in obtaining accurate results and overcome the problems associated with past holders.

It is, therefore, an object of this invention to provide a dynamic functional optical imaging system which can be utilized in conjunction with the study of biological objects and utilizing a non-rigid object holder therewith.

It is another object of this invention to provide a non-rigid holder for use in medical procedures, especially breast examinations.

It is the further object of this invention to provide a dynamic functional optical imaging mammoscopy system which overcomes the problems of past cancer diagnostic and screening techniques.

SUMMARY OF THE INVENTION

The objects set forth above as well as further and other objects and advantages of the present invention are achieved by the embodiments of the invention described hereinbelow.

The present invention incorporates a non-rigid biological object holder within a dynamic functional imaging system, and, in particular, a dynamic functional mammoscopy system which is capable of performing accurate breast cancer screening. It should be realized, however, that this holder is not limited to use as only a breast holder and may be used, for example with other parts of the body such as the abdomen, muscles or even an entire body as in the case of an infant or other biological objects. Within the system of this invention, a biological object such as the breast can be placed between two flexible, elastic, resilient membranes that form parts of two inflatable bags. A single flexible member may also be used as part of the present invention. The examination takes place under controlled external pressure and thereby overcomes many of the problems associated with past hard plate holders as used in mammography or optical mammoscopy systems. The external pressure control together with the optical system of the dynamic functional imaging system operates in a synergistic fashion with the non-rigid holders of the present invention. The design of the present invention, made up of a number of different embodiments, overcomes the problems associated with past breast cancer screening techniques, examples of which are described above, and enables the breast cancer screening technique to take place in a safe, inexpensive and highly accurate manner.

BRIEF DESCRIPTION OF THE DRAWINGS

FIG. 1 is a schematic representation, illustrating a side view partially in cross-section, of the dynamic functional mammoscopy system of this invention incorporating therein the non-rigid holder of this invention;

FIG. 2 is a schematic representation, illustrating a front view partially in cross-section, of the dynamic functional mammoscopy system of this invention shown in FIG. 1 incorporating therein the non-rigid holder of this invention and also showing an alternate illumination system in the dashed box;

FIG. 3 is a block diagram of the major electronic components of the dynamic functional mammoscopy system of this invention;

DETAILED DESCRIPTION OF THE PREFERRED EMBODIMENTS

Figure 4:
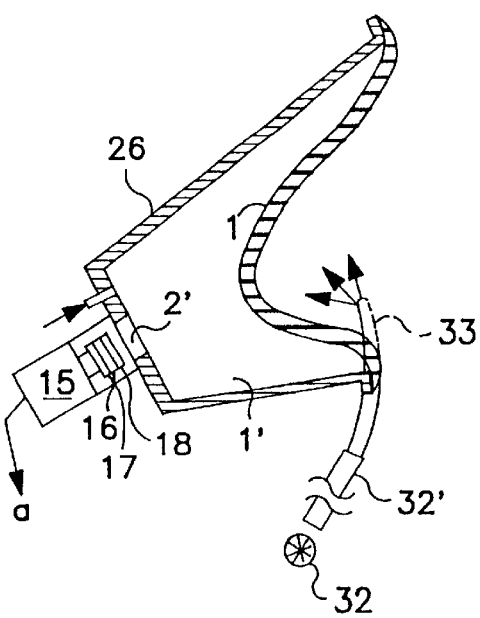
FIGS. 4 and 5 represent the dynamic functional mammoscopy system of this invention incorporating therein alternate embodiments of the non-rigid holder of this invention.

The apparatus making up the DFOM with the non-rigid or soft holder incorporated therein is described with respect to FIGS. 1–3. Reference can be made to the above cited U.S. patent application Ser. Nos. 08/565,747, 08/678,786 and 08/664,189 for a basic understanding of dynamic functional imaging systems and its use in mammoscopy. These applications, all commonly owned by assignee, and any patents which issue therefrom are incorporated herein by reference. Furthermore, for purposes of clarity, like references numerals will be used throughout the description and drawings to refer to substantially identical components.

With the present invention, and referring to FIGS. 1 and 2 of the drawings, the object or breast 10 under examination is softly compressed between two non-rigid elastic resilient membranes 1 and 4 (considered the soft holder) attached to transparent plates 2 and 3, preferably made of Plexiglas® to create two inflatable bags 1' and 4', respectively. As shown in FIG. 2, the membranes 1 and 4 are framed by nontransparent members or plates 5 and 5' which still enable transparent plates 2 and 3 to be adjusted with respect to each other. This type of non-rigid holder substantially eliminates any discomfort to the patient during examination as previously encountered with the rigid holders necessitated by prior mammography procedures.

It is possible with the present invention to examine each breast individually with a single non-rigid holder or, preferably to utilize a pair of such holders and associated components in a manner similar to that described in U.S. patent application Ser. No. 08/664,189. It should be further realized that the holders may also be configured to old other parts of the body (biological objects) or even an entire body as in the case of an infant. A near-infrared (NIR) light source 14 is associated with membrane 4 and transilluminates the lower bag 4', object (the breast 10) and the upper bag 1' covering the breast. The optical recording system 12 includes a CCD camera 15 (with zoom lens 16) and dynamic interface board (frame grabber) 23 for acquisition of the sequences of the optical frames for transmission to a conventional computer 25, which may be a personal computer (PC). As shown in FIG. 3, the computer 25 via PC interface board 24 and the pneumatic unit 20 controls the pressures created by compressor 21 in the both bags 1' and 4' and via electronic interface unit 22 controls the illumination conditions created by the illuminator or light source 14. The recording system 12 is utilized for measuring and analyzing relative spatial-temporal variations of the intensity of the light passed through the breast 10 due to the modulation of the optical parameters (absorbance and scattering) of the breast tissues by its physiological functioning (blood, oxygenation and metabolic rate redistribution).

In order to formulate continuous temporal sequences of the optical images, they are recorded at intervals differentially small as compared with time constants of the tissues physiological dynamics, that is, several frames per second is a sufficient rate. The frames sequences are accumulated in the computer memory. The relative temporal variation of the intensity, that is, the temporal signature (TS) is calculated two ways: 1) by subtracting the first frame from any sequential one and normalizing the difference on the intensity distribution on the first frame or 2) applying the logarithmic derivative. To reveal the pathological functional contrast the Functional Segmentation (FS) is applied by various options, including but not limited to, the cross-correlation of the FS over the image.

As mentioned above, the soft holder of this invention is substantially more effective than past holders for examination of functional physiological parameters of soft tissues since it is the pressure applied to the object under examination that controls the tissues' hemodynamics, and thereby, such related parameters as tissue elasticity, oxygenation, metabolic rate, skin perspiration, etc. Furthermore, since the soft holder of this invention is naturally compatible with soft tissue and does not create pain or any discomfort for patients it is a substantial advancement over past holders used in breast examination.

The most effective application of soft holder of this invention is in breast examination with the dynamic functional optical imaging (DFOI) in a transillumination or reflectometry scheme. The soft holder is also applicable for dynamic functional imaging of the abdominal cavity (in reflectometry scheme) and muscles (both transillumination and reflectometry schemes). The present soft holder can also be utilized for gentle immobilization during DFOI examination of the brain, abdomen, and even the whole body of newborns in baby-incubators.

Figure 6:
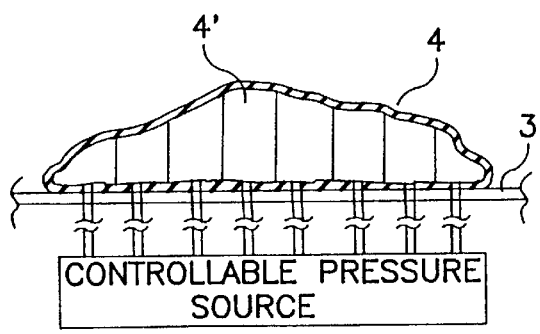
FIG. 6 is a cross sectional view of a resilient membrane having compartments therein to more controllably regulate pressure.

Referring once again to FIGS. 1 and 2 of the drawings, a latex film with a thickness of 30–150 μm is preferred for the upper measuring membrane 1. Such latex being stretched and thereby made thinner (almost in half) after inflation of the bag 1' so as to become sufficiently transparent for the functional imaging to take place when the spatial resolution is not so critical. In fact, the stretched latex interferes no more with the light propagation than the diffusive thin layer of the skin. The low bag membrane 4 is used for shaping of the breast during the examination and to push the pathology closer to the upper breast surface. Therefore, a thicker latex film having a thickness of approximately 100–300 μm, or plastic film (for example, polyethylene film with thickness of 20–50 μm) can be used. As shown in FIG. 6 of the drawings, the lower bag 4' can be made from several sections of material thereby even further controlling compression. This gives rise to the possibility of selectively compressing portions of the breast or object in order to control the distribution of thickness of the breast or other object under investigation or to equalize the thickness of the breast being compressed in the soft holder. It is especially useful to concentrate compression of the breast adjacent the area of pathology. Equalization of the thickness of the object (breast) directly results in effecting the intensity of the light passing through the object, which is important for the necessary expansion of the dynamic range of the recording system, as described below. It should be further noted that the soft holders can be rotated in order to pass light through the breast in any direction, for example, the top instead of the bottom. Even further, duplicate light sources and receivers can be associated with each bag, if so desired. In addition, the membranes can not only be made of latex, but also any other suitable transparent film such as polyethylene.

Prior to the examination process, the breast is placed over the low bag 4' which is initially inflated up to 30–80 mmHg so that the edge of the supporting transparent Plexiglas® plate 3, framed by the metal plate 5, is positioned adjacent the chest wall. An optimum breast positioning angle between supporting plate 3,5 and support 6 is approximately 20–30 degrees. Thereafter, the breast is covered by the latex membrane 1 of the upper bag 1' which is inflated up to an initial pressure of approximately 2–5 mm Hg. This action is accomplished by rotating plate 2 about the horizontal axis 7 in order to position membrane 1 against the breast. Once in position it can be secured in place with any suitable clamping mechanism 8. Then the lower bag 4' is inflated up to approximately 100–200 mm Hg for the breast shaping. As a result thereof, pressure in the upper bag 1' is increased up to 5–10 mm Hg just before the start of the breast examination. During examination, both bags 1' and 4' are inflated in a controlled fashion by control valves 13 and 13' under pressuremeters 11 and 19 which monitor the operation.

The soft holder of this invention, with elastic resilient membranes 1 and 4. is an active and interactive part of both the DFOM method and apparatus of the present invention as described below. During the initial part of the examination a smooth compression of the breast takes place by slow inflation (0.5–2 mm Hg/sec) of the upper bag 1' from the initial pressure of 5–10 mmHg up to approximately 10–60 mm Hg (this pressure being more than one order of magnitude less than level of the pressure applied in mammography). The temporal valuation of the optical image during this procedure reveal differences (the contrast) in the tissues' compressibility. The less compressible (palpable) area decreases less of the thickness and so there is less of an increase of the transparency during the compression. In nonpalpable cases another mechanism, that is, the difference in the tissues mechanical impedance determined by the condition of physiological liquids (blood and lymph), that is, venular and lymphatic resistivity against blood and lymph repulsion can reveal the pathology. Another possible scenario would be to increase the pressure rapidly, for example, 3–10 mm Hg for one second and just thereafter investigate tissue reaction during approximately 20–40 seconds at the same increased pressure. Such a procedure creates a dynamic contrast between pathological and normal tissues. It is also possible to combine several sequential pressure steps up, for example, four steps up of approximately 3–7 mm Hg/sec each, starting from initial level of 5–10 mm Hg, with a duration of the pressure plateau 30–40 sec between the steps to investigate the image valuation. Other alternate steps can also be applied. The period of the pressure variation described above is close to that of spontaneous oscillations of blood content into the breast so it is possible to synchronize the external pressure variations with this internal oscillation in real time based upon feedback from the changes in light intensity. Such interactive procedure substantially increases the possibility to reveal the pathology.

The pressure protocol can also include an investigation of the DFOM-image evaluation after one or more pressure increases or jumps, or after completion of the final pressure jump or increase, that is when the pressure is stabilized for 3–10 minutes at a "pressure plateau." During the plateau phase, under constant pressure, evaluation is performed at the constant pressure in order to determine possible contrast in long term tissue reactivity. After the above investigation or evaluation has taken place, the constant or pressure plateau can be decreased by sequential downward steps or jumps, a single decrease in pressure or a sequence of pressure drops until the initial pressure of 5–10 mmHg has been reached. Thereafter a sequential investigation or evaluation can take place at the 5–10 mmHg pressure level for 3–10 minutes to reveal any possible contrast in long term tissue relaxation.

Besides the external pressure tests conducted with the latex membranes 1 and 4 described above, other stimuli can be utilized such as hypoxy, hypercopny, glucose uptake and especially sensory tests from the nipple (the main sensory area of the breast). The image valuation after such tests in the soft holder will include two modalities. It is possible to see from the basic analysis presented below that the relative variation of the intensity passing throughout the breast in the soft holder $\Delta I/I(x,y,t,\lambda)$ is equal to $$\Delta I/I(x,y,t,\lambda)=K \times D(\Delta K/K+\Delta D/D)$$

where (x,y) are coordinates of the pixel, t represents time, λ represents wavelength of the light, D represents the thickness of the compressed breast, K, the light attenuation coefficient in multiple scattering media is equal to the square root of (3 Ks×Ka), where Ks is light scattering coefficient, Ka is the absorbance coefficient. The first contribution, $\Delta K/K$ reflects the modulation of the tissues optical parameters by blood and oxygenation changes initiated by the tests directly. The second contribution, $\Delta D/D$, reflects differential variations of the breast volume and shape due to redistribution of the blood and lymph in the breast initiated by the tests.

It is also important to realize that utilization of the non-rigid holder of this invention opens up the possibility of further pathology projection. For example, the relative temporal variations of the light intensity transmitted through the object such as the breast $\Delta I/I$ (x,y,t) are proportional to the variations of the light attenuation by the breast tissues $\Delta$(K X D), where K(x,y,t) is the tissues attenuation coefficient, combining the scattering and the absorption, and D(x,y,t) is the thickness of the breast; $\Delta$(K X D) consists of the two contributors $\Delta K$ X D and $\Delta D$ X K: the first one is responsible for the conventional optical diffusion projection and the additional second one represents a new opportunity—dynamic optical deformoscopy (DOD). DOD contrasts the pathology based on the differences in the dynamical compressibility of the tissue. It is, in actuality, the mechanical projection of the pathology from the tissue's depth so the spatial resolution is not restricted by light diffusion. This new, additional modality of the DFOM is similar to palpation but with the advantages of being objective and, even more importantly, being dynamic imaging modality which reveals not only static masses, but also a dynamical pattern of the tissue's compressibility. This pattern reflects the corresponding dynamic functional pattern of the blood (and lymph) circulation in the mammary gland or object under examination. Such dynamic "palpascopy" opens the possibility of recording data with high accuracy and storing, in a computer memory, dynamic "molds" of the mammary gland, specific to various physiological conditions.

For effecting the above, a coherent laser source and system for projecting some type of interference pattern (grating or grid) on the membrane surface, covering the breast, are necessary. In addition it is necessary to utilize CCD for the recording of dynamical changes of the grating or the grid parameters during breast compression or its spontaneous behavior. Such a procedure and system gives rise to the possibility for the Dynamic Optical Deformascopy of the breast or other part of the body in a reflective mode; the sensitivity being sufficient to record blood redistribution dynamics in the skin as an alternative to the rather expensive infrared thermovision procedure.

By application of an oscillating pressure it is possible to initiate periodic changes of breast deformation $\Delta D(x,y)$, recorded by DOD. This opens the possibility of obtaining distribution of absolute values for the attenuation coefficients K(x,y) for different wavelengths and distribution of the blood volume, and the oxygination and metabolic rate by recording relative changes of the intensity of light, transilluminating breast, $\Delta I/I(x,y)$ K(x,y) X $\Delta D(x,y)$. The periodical variation of deformation lends itself to increased accuracy by intensity synchronous recording.

Figure 8:
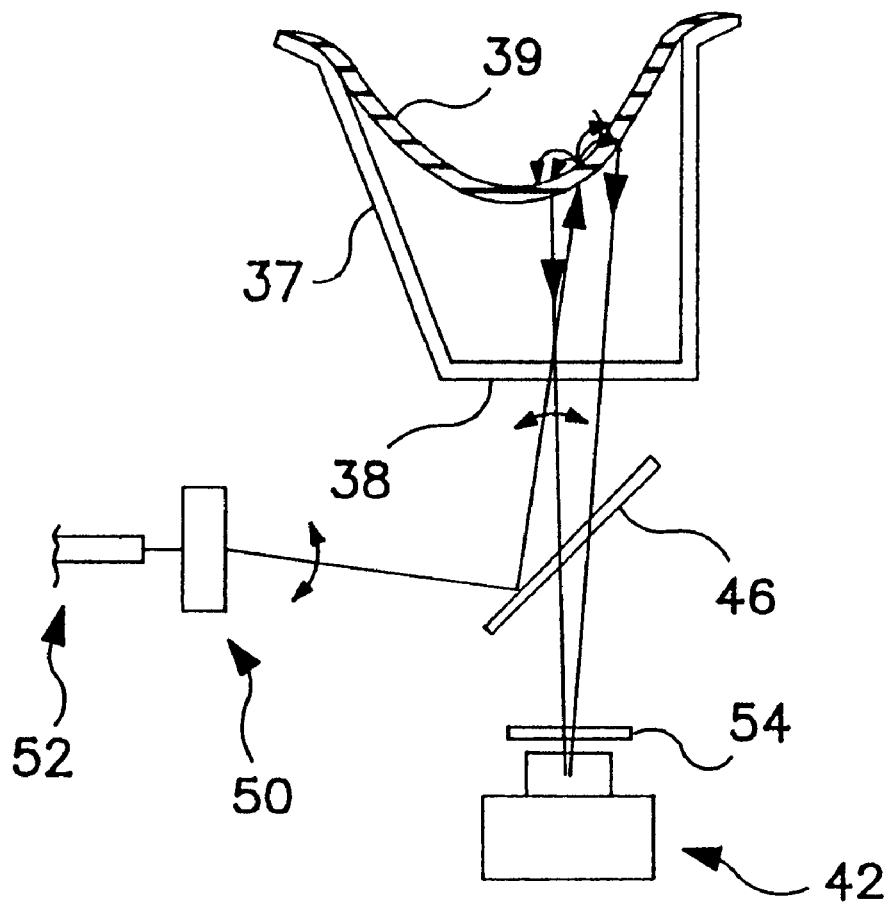
FIG. 8 is a schematic representation of a still further embodiment of the present invention which incorporates a single resilient member and a scanning system.

The present invention also incorporates therein, but is not limited to further embodiments as set forth below. For example, variations in the type of illuminators used, two of which are shown in the drawings. One being the LED array 14 shown in FIG. 1 and the other being illustrated in the dashed box as fiberoptic illuminator 9. In addition, a scanning mechanism as shown in FIG. 8 can also be used.

The LED array 14 is made up of the several (up to 25) sections whose intensities are independently controlled by electronic unit 22 to equalize the intensity distribution on the first frame before test applications begin. It is necessary to expand the dynamic range of the recording system to get high accuracy. Examples of ranges of four spectral bands picked are at wavelengths of 0.6–0.78 $\mu$m, 0.78–0.82 $\mu$m, 0.82–0.93 $\mu$m, and 0.93–1.2 $\mu$m. The range of 0.6–0.78 $\mu$m is specific for the venular blood absorbance that is much stronger in the cancerous tissues. This band is very sensitive to changes in the tissues oxygenation. The band range of the isobestic point 0.78–0.82 $\mu$m for oxy- and dezoxyhemoglobin absorbance is sensitive only to changes of the blood volume and so it is a good reference for the band 0.6–0.78 $\mu$m and 0.82–0.93 $\mu$m to separate contributions of the blood volume and the oxygenation changes. The band in the range of 0.93–1.2 $\mu$m is sensitive to water content and temperature, those both being increased in cancerous tissues versus normal ones. For the above purpose, the LED's, with the four wavelengths mentioned, were distributed by groups along the illuminator 14. Similar LED's (one from each group) are switched alternatively to obtain one multispectral frame, the four spectral subframes being recorded sequentially. For example, for the multispectral dynamic imaging with a rate of one frame per second, three different spectral subframes per second should be recorded. The intensity of illumination was set at no greater than 30 m W/cm$^2$/sec to exclude any heating discomfort for the patient. As shown clearly in FIG. 2, a nontransparent diaphragm 27, adjustable to the breast size, was used to protect against leakage of the illuminating light next to the breast.

Use of the alternate fiberoptic illuminator 9 is also shown in FIG. 2 in the dashed box. Fiberoptic illuminator 9 includes a light source such as halogen lamp 28, a filter wheel 29 with alternately changeable filters 30 controlled by PC-board 24 corresponding to the spectral bands explained above, reflective thermofilter 31 and fiberoptic guide 32.

The recording system for the DFOM of this invention, as explained above, obtains maximum accuracy in measuring relative temporal changes of the intensity along the optical image. For this purpose, the CCD with a maximum dynamic range should be utilized. To increase the dynamic range, a CCD with a large size of the pixel, 128×128 pixels are appropriate, since Dynamic Functional Optical Imaging is less reliant on spatial resolution than in morphological imaging. For additional increase of the dynamic range, the intensity in the first frame should be maximally equalized. For this purpose, in addition to equalization by the controlled multisectional illuminator 14 and equalization of the compressed breast thickness by controlled inflation of a multisectional lower bag 4', as were explained above, controlled optical transparency can be obtained by the use of, for example, liquid crystal film 18 for final intensity equalization before the CCD.

It is also very important to exclude scattered light, especially its temporal variation, during operation of the system. Therefore, a nontransparent screen 26 with transparent window 2 for the CCD and spectral filter 17 capable of eliminating light with wavelengths of less than 0.6 $\mu$m (that cannot pass through the breast) are utilized with the present invention. The membrane 1 is attached to the perimeter of metal frame 26 adjacent the chest wall for breast examination.

Figure 5:
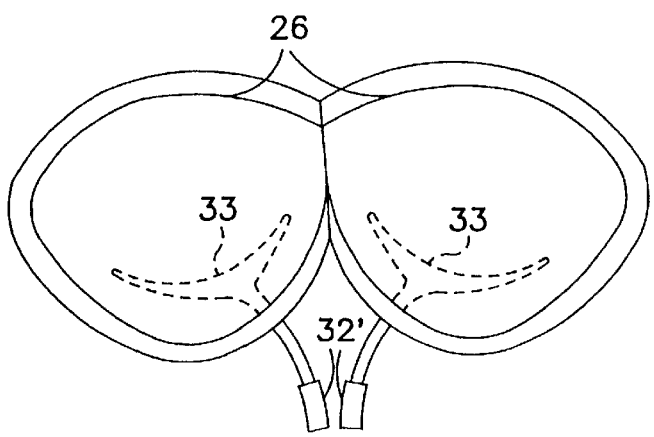

In addition to the above, front view projection is very important for breast examination with the present invention since the breast functioning and morphology are symmetrical around the nipple. The design of the non-rigid or soft holder of this invention for front examination is shown in the embodiments of FIGS. 4 and 5. In this case, the latex membrane 1 compresses the breast against chest wall of the patient. In order to provide for the possibility of such compression the support 26 should be attached to the chest wall or other part of the body under investigation by any suitable securing means such as a strap or adhesive may be used with the present invention. For illumination, a transparent plastic adapter 33, taken from a set of adapters of different size and shape determined by various breast sizes and shapes, is placed under the breast. The adapter 33 is connected with fiberoptic guide 32' providing light from light source 32 as shown in FIGS. 4 and 5. The optical recording system 12 is similar to the system shown in FIG. 1 and is located adjacent a transparent window 2'.

Figure 7:
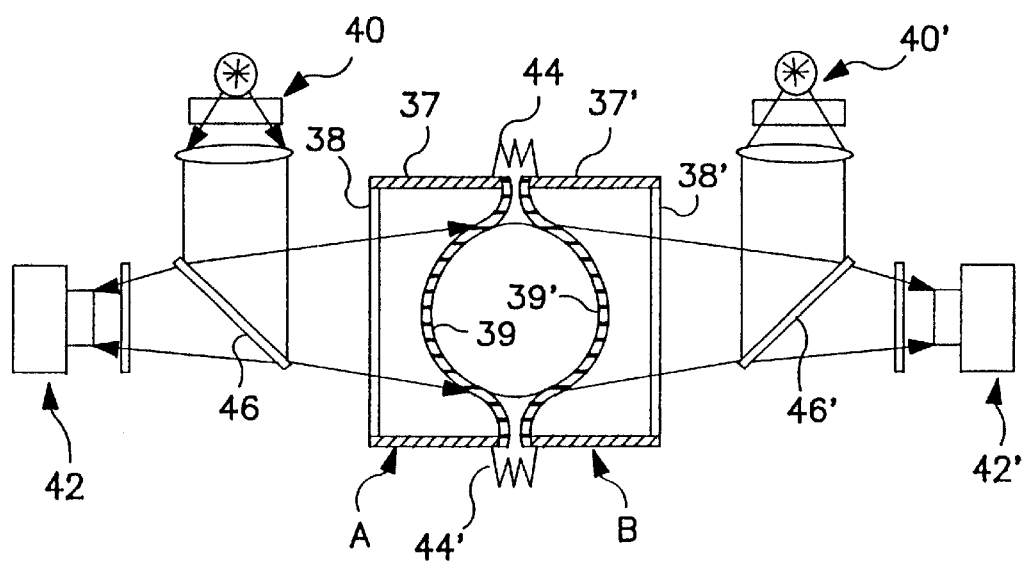
FIG. 7 is a schematic representation of a further embodiment of the present invention which incorporates therein the use of a symmetrical non-rigid holder.

Reference is now made to FIG. 7 of the drawing which illustrate a further embodiment of the present invention showing a symmetrical design of the non-rigid holder of this invention incorporated within a DFOM apparatus. More specifically, in this embodiment, the resilient membranes 39 and 39' are substantially identical and formed of two separate "mirror image" components A and B. These components are made of non-transparent frame portions 37 and 37', respectively, and transparent windows 38 and 38', respectively, to which the resilient membranes 39 and 39' are attached. The transparent windows are in optical alignment with the optical source and detecting systems 40, 40' and 42, 42'. The membranes 39 and 39' are controllably inflated by a pressure system (not shown) similar to the system used for controllably inflating membranes 1 and 4 within FIG. 1 of the drawings.

The non-rigid holder of the type shown in FIG. 7 of the drawings is primarily used with a patient lying down and when the breast symmetry around the nipple is not disturbed by its weight. The two components A and B are held together by flexible members 44 and 44' which enable the frames to be adjustably moved with respect to one another when placed around a breast or other object to be examined. In the embodiment shown in FIG. 7 of the invention, there is a symmetrical disposition of the optical or light sources 40 and 40' and the detecting systems 42 and 42'. This set up enables both sides of the object or breast to be examined simultaneously by alternately (frame by frame) switching of the light sources 40, 40' and detecting systems 42, 42'. The light sources and detecting systems used with this embodiment of the invention are identical in design and incorporates therein similar components as shown with respect to FIG. 1 the drawings. In conjunction therewith, beam directors (partially reflective) 46 and 46' are utilized to both direct and redirect the light source radiation to and from the object under examination. It is clear in this embodiment that the light source(s) and light detector(s) are located on the same side.

Reference is now made to FIG. 8 of the drawings which illustrates an embodiment of the invention which includes a single resilient member 39 attached to a nontransparent frame 37 and a transparent window 38 together with a scanning system 50 for light emission from source 52. The scanning system enables the light source to be in the form of a single source scanned over a preselected area of the breast or object under examination. A detecting system is incorporated within the embodiment of FIG. 8, preferably on the same side of the breast as the source. A partially reflective beam director 36 is utilized therewith as with the embodiment of FIG. 7.

In the reflective mode, the light source is located on the same side and is used to record a radial distribution of intensity around the illuminating beam to obtain the necessary distribution of physiological pigments (blood, oxygen, etc.) over a preselected depth in the illuminated area.

Special optical shielding (shadowing) of the central part of the image before the CCD, that is, the bright illuminated area of the beam impacting the breast surface may be required to exclude overloading of the CCD. A liquid crystal transparent (or other) non-linear filter 54 with inverse transparency dependent on the intensity of the light source can be placed before the CCD 42. The general operation of the embodiments of the invention shown in FIGS. 7 and 8 are similar to those described with reference to the embodiments of FIGS. 1 and 2.

Figure 9:
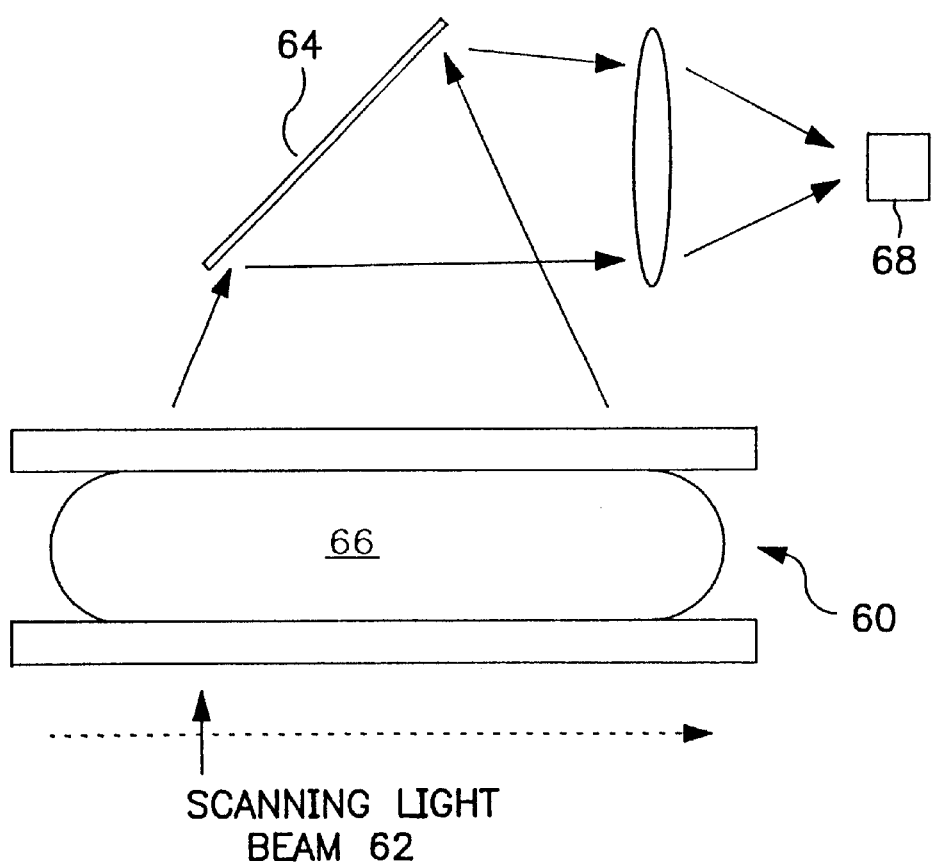
FIG. 9 is a schematic representation of a beam scanning system used with a further embodiment of the present invention.

In the transillumination mode, the non-rigid holder is utilized in combination with a single channel photo detector, placed on the other side of the breast to record integral intensity of the transilluminating light for different locations of the illumination beam. This enables the pathology to be investigated which is located closer to the illuminating side of the breast. Reference is made to FIG. 9 of the drawings for a schematic illustration of such a mammoscopy set up 60 having a scanning light beam 62. A semitransparent mirror 64 enables the combination of a single channel photodetection of integral intensity transmitted through the breast 66 with the recording of breast images by a CCD camera 68.

Although the invention has been described with reference to particular embodiments, it will be understood that this invention is also capable of further and other embodiments within the framework of this invention.

What is claimed is:

1. A non-rigid object holder assembly for use in examination of an object, said object holder assembly comprising:

a support;

first and second members movably mounted with respect to each other and said support;

means operably connected to said first and second members for controllably moving said members with respect to each other and said support;

a first resilient membrane attached to said first member and a second resilient membrane attached to said second member, said first and said second resilient membranes forming first and second inflatable components for holding the object therebetween;

means operably connected to said first and said second inflatable components for controllably inflating each of said inflatable components;

a source of electromagnetic radiation optically associated said inflatable components for providing a beam of light to the object;

said first and said second resilient membranes and portions of both said first and second members being transparent to said electromagnetic radiation, and an optical detecting system optically aligned with said source of electromagnetic radiation for receiving said electromagnetic radiation passing through and/or being backscattered from the object.

2. The non-rigid object holder assembly as defined in claim 1 herein said first resilient membrane is used to shape the object and has a predetermined thickness and said second resilient membrane has a thickness which is less than said redetermined thickness.

3. The non-rigid object holder assembly as defined in claim 2 wherein said source of electromagnetic radiation is located adjacent said first resilient membrane and said optical detecting system is located adjacent said second resilient membrane.

4. The non-rigid object holder assembly as defined in claim 3 wherein said source of electromagnetic radiation is also located adjacent said first member, and said optical detecting system is also located adjacent said second member.

5. The non-rigid object holder assembly as defined in claim 4 further comprising a nontransparent diaphragm positioned adjacent said first and second resilient membranes.

6. The non-rigid object holder assembly as defined in claim 3 wherein said another source of electromagnetic radiation is located adjacent said second resilient membrane and another optical detecting system is located adjacent said first resilient membrane.

7. The non-rigid object holder assembly as defined in claim 2 wherein said thickness of said first resilient membrane is approximately 100–300 microns and said thickness of said second resilient membrane is approximately 30–150 microns.

8. The non-rigid object holder assembly as defined in claim 1 wherein said first resilient membrane is made in sections.

9. The non-rigid object holder assembly as defined in claim 1 further comprising means for securing said first and second members in a predetermined position with respect to each other.

10. The non-rigid object holder assembly as defined in claim 1 wherein said source of electromagnetic radiation is in the form of an LED array.

11. The non-rigid object holder assembly as defined in claim 9 further comprising means for controlling the intensities of each LED in said array and wherein said array produces electromagnetic radiation of at least two different spectral bands.

12. The non-rigid object holder assembly as defined in claim 11 wherein there are four separate spectral bands of electromagnetic radiation, one being approximately 0.6–0.78 microns, another being 0.78–0.82 microns, another being approximately 0.82–0.93 microns and another being approximately 0.93–1.2 microns.

13. The non-rigid object holder assembly as defined in claim 1 wherein said source of electromagnetic radiation is in the form of a fiber optic illuminator.

14. The non-rigid object holder assembly as defined in claim 1 wherein said non-rigid object holder is in combination with a system for performing dynamic functional imaging of the object.

15. The non-rigid object holder assembly as defined in claim 14 wherein the object is a human breast.

16. The non-rigid object holder assembly as defined in claim 1 wherein said first and second inflatable components are symmetrical.

17. The non-rigid object holder assembly as defined in claim 16 wherein said source of electromagnetic radiation is also located adjacent said first member, said optical detecting system is also located adjacent said second member, and said first and said second resilient membranes and portions of both said first and second members are transparent to said electromagnetic radiation.

18. A non-rigid object holder assembly for use in examination of a portion of an object, said object holder assembly comprising:
   a support, said support being capable of being attached to the object adjacent the portion of the object being examined;
   a resilient membrane attached to said support and said resilient membrane forming an inflatable component;
   means operably connected to said inflatable component for controllably inflating said inflatable component;
   a source of electromagnetic radiation for providing light for transilluminating the object; and
   an optical detecting system optically aligned with said source of electromagnetic radiation for receiving said electromagnetic radiation passing through the object.

19. The non-rigid object holder assembly as defined in claim 18 wherein the object is a breast and said source of electromagnetic radiation is operably connected by a fiber optic component to an adapter inserted behind a portion of the breast postioned against said resilient member between a chest wall and the breast.

20. The non-rigid object holder assembly as defined in claim 19 wherein said non-rigid object holder is in combination with a system for performing dynamic functional imaging of the object.

21. The non-rigid object holder assembly as defined in claim 20 wherein the object is a human breast and said resilient membrane shapes the breast against a chest wall.

22. A method of using a non-rigid holder assembly during an examination of the object by dynamic functional imaging, the non-rigid holder assembly having a first inflatable component including a first resilient membrane and a second inflatable component including a second resilient membrane, said method comprising the steps of:
   inflating said first component to a first predetermined pressure;
   placing the object adjacent said first resilient membrane;
   moving said second resilient membrane with respect to said first resilient membrane such that said second resilient membrane substantially covers the object;
   fixing the position of said second resilient membrane with respect to said first resilient membrane;
   inflating said second component to a second predetermined pressure which is less than said first predetermined pressure;
      substantially increasing said first predetermined pressure of said first component in order for said first resilient membrane to shape the object prior to the examination; and
      controllably inflating said first and second components during the examination.

23. The method of using the non-rigid holder assembly as defined in claim 22 further comprising the step of gradually inflating said second component during the initial part of the examination.

24. The method of using the non-rigid holder assembly as defined in claim 23 wherein said step of gradually inflating said second resilient inflatable membrane takes place at approximately 0.5–2 mmHg/sec. from an initial pressure of 5–10 mmHg to 10–60 mmHg.

25. The method of using the non-rigid holder assembly as defined in claim 22 further comprising the steps of:
   rapidly inflating said second component to a third predetermined pressure; and
   maintaining said third predetermined pressure for a preselected period of time during the examination.

26. The method of using the non-rigid holder assembly as defined in claim 22 further comprising the steps of:
   inflating said second components in a series of several sequential steps to a series of new predetermined pressures; and
   maintaining each of the new predetermined pressures for a preselected period of time during the examination.

27. The method of using the non-rigid holder assembly as defined in claim 26 wherein said each of said several sequential predetermined pressures are approximately 3–7 mmHg with said preselected time being approximately 30–40 seconds between said sequential steps.

28. The method of using the non-rigid holder assembly as defined in claim 26 wherein said preselected period of time is approximately 3–10 minutes.

29. The method of using the non-rigid holder assembly as defined in claim 22 wherein said first predetermined pressure is approximately 30–80 mmHg.

30. The method of using the non-rigid holder assembly as defined in claim 29 wherein said second predetermined pressure is approximately 2–5 mmHg.

31. The method of using the non-rigid holder assembly as defined in claim 30 wherein said substantially increased predetermined pressure is approximately 100–200 mmHg.

* * * * *